US008889629B2

(12) United States Patent
Scalfaro et al.

(10) Patent No.: US 8,889,629 B2
(45) Date of Patent: Nov. 18, 2014

(54) USE OF A CYCLIC UNDECAPEPTIDE FOR THE PREPARATION OF A MEDICAMENT FOR ADMINISTRATION DURING MYOCARDIAL ISCHAEMIC EVENTS

(75) Inventors: Pietro Scalfaro, Lausanne (CH); Jean-Maurice Dumont, Pully (CH); Grégoire Vuagniaux, Lausanne (CH)

(73) Assignee: Debiopharm International SA, Lausanne (CH)

( * ) Notice: Subject to any disclaimer, the term of this patent is extended or adjusted under 35 U.S.C. 154(b) by 1359 days.

(21) Appl. No.: 11/794,245

(22) PCT Filed: Jan. 10, 2006

(86) PCT No.: PCT/EP2006/050140
§ 371 (c)(1),
(2), (4) Date: Jul. 16, 2007

(87) PCT Pub. No.: WO2006/072639
PCT Pub. Date: Jul. 13, 2006

(65) Prior Publication Data
US 2009/0023640 A1 Jan. 22, 2009

(30) Foreign Application Priority Data
Jan. 10, 2005 (EP) ..................................... 05000357

(51) Int. Cl.
*A61K 38/13* (2006.01)
*A61K 38/12* (2006.01)

(52) U.S. Cl.
CPC ....................................... *A61K 38/13* (2013.01)
USPC .......................... 514/20.5; 514/15.6; 514/16.4

(58) Field of Classification Search
CPC ............................... A61K 38/12; A61K 38/13
USPC ....................................... 514/20.5, 15.6, 16.4
See application file for complete search history.

(56) References Cited

U.S. PATENT DOCUMENTS 6,201,165 B1 * 3/2001 Grant et al. ........................ 800/3
6,492,401 B1 * 12/2002 Hamanaka et al. ............ 514/359
6,790,935 B1 9/2004 Mutter et al.
6,927,208 B1 * 8/2005 Wenger et al. ..................... 514/9

FOREIGN PATENT DOCUMENTS

WO WO 00/01715 1/2000

OTHER PUBLICATIONS

Acute myocardial infarction from http://www.medterms.com/script/main/art.asp?articlekey=7489, pp. 1-3. Accessed Jun. 11, 2009.*
Coronary Angioplasty from http://www.nhlbi.nih.gov/health/dci/Diseases/Angioplasty/Angioplasty_WhatIs.html, p. 1. Accessed Jun. 11, 2009.*
Fibrinolysis from http://www.nlm.nih.gov/MEDLINEPLUS/ency/article/000577.htm, pp. 1-2. Accessed Jun. 11, 2009.*
Intravenous injection from http://www.merriam-webster.com/medical/intravenous, pp. 1-2. Accessed Jun. 11, 2009.*
Intraarterial injection from http://www.merriam-webster.com/medical/intraarterial, pp. 1-2. Accessed Jun. 11, 2009.*
Intracoronary injection from http://www.merriam-webster.com/medical/intracoronary, pp. 1-2. Accessed Jun. 11, 2009.*
Di Lisa et al, "Opening of the Mitochondrial Permeability Transition Pore Causes Depletion of Mitochondrial and Cytosolic NAD$^+$ and Is a Causative Event in the Death of Mycocytes in Postischemic Reperfusion of the Heart", Journal of Biological Chemistry, vol. 276, No. 4, Jan. 26, 2001, pp. 2571-2575.
Hansson et al, "the Nonimmunosuppressive Cyclosporin Analogs NIM811 and UNIL025 Dislplay Nanomolar Potencies on Permeability Transition in Brain-Derived Mitochondria", Journal of Bioenergetics and Biomembranes, Plenum Publishing, New York, NY, US, vol. 36, No. 4, Aug. 2004, pp. 407-413.
Neimann et al, "Close Association Between the Reduction of Myocardial Energy Metabolism and Infarct Size: Dose-Response Assessment of Cyclosporine", Journal of Pharmacology and Experimental Therapeutics, vol. 302, No. 3, Sep. 2002, pp. 1123-1128.
Hausenloy et al, "Inhibiting mitochondrial permeability transition pore opening: a new paradigm for myocardial preconditioning?", Cardiovascular Research, vol. 55, No. 3, Aug. 15, 2002, pp. 534-543.
International Search Report mailed Jun. 1, 2006 in PCT/EP2006/050140.
Squadrito et al. "Cyclosporin-A reduces leukocyte accumulation and protects against myocardial ischaemia reperfusion injury in rats" Eur. J. Pharmacol. 364:159-168 (1999).

* cited by examiner

*Primary Examiner* — Julie Ha
(74) *Attorney, Agent, or Firm* — Nixon & Vanderhye PC

(57) ABSTRACT

The invention relates to the use of a cyclic undecapeptide, with the structure in formula (I), for the preparation of a medicament for administration during a myocardial ischaemic event.

19 Claims, 2 Drawing Sheets

Figure 1:
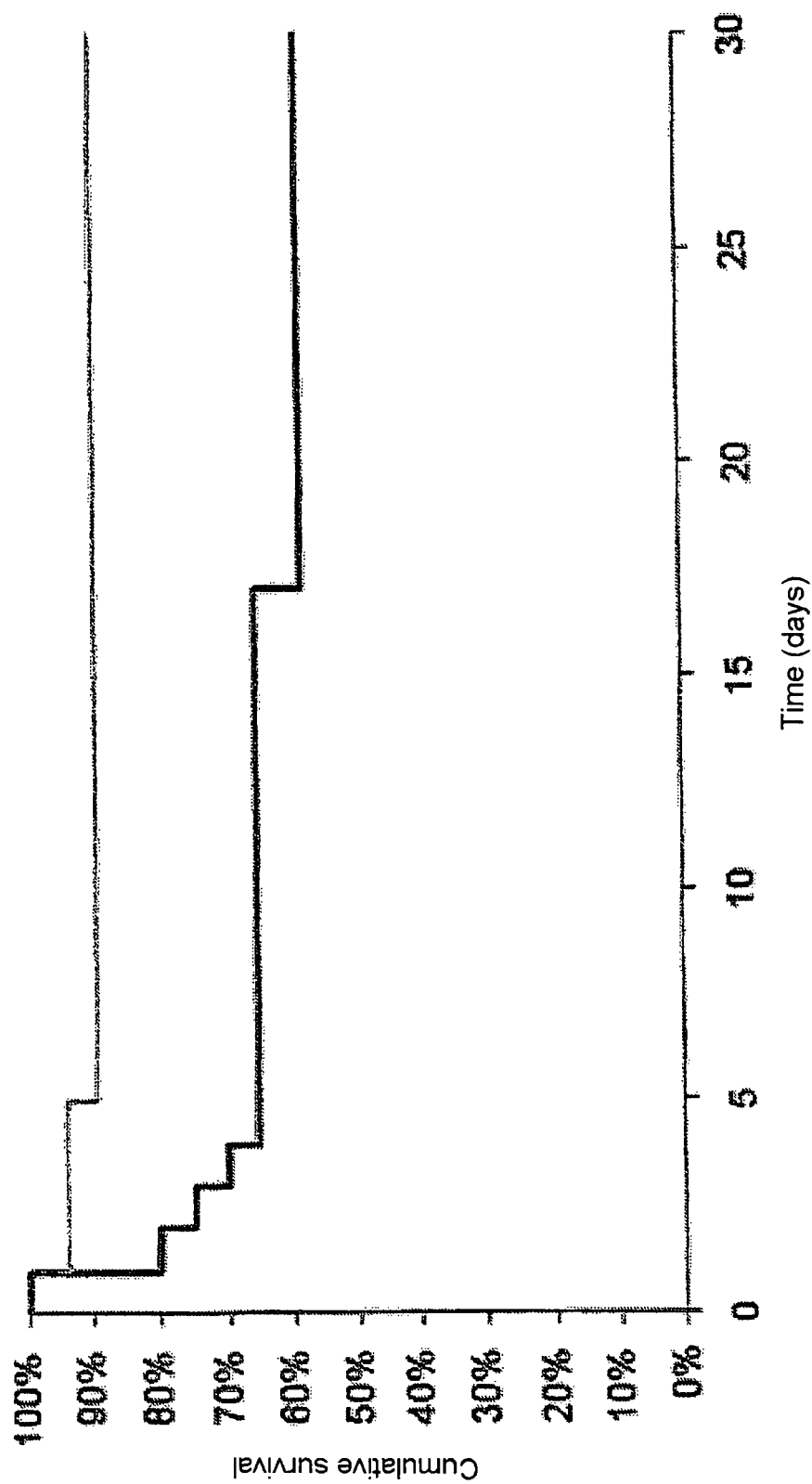

USE OF A CYCLIC UNDECAPEPTIDE FOR THE PREPARATION OF A MEDICAMENT FOR ADMINISTRATION DURING MYOCARDIAL ISCHAEMIC EVENTS

This application is the US national phase of international application PCT/EP2006/050140 filed 10 Jan. 2006 which designated the U.S. and claims benefit of EP 05000357.3, dated 10 Jan. 2005, the entire content of which is hereby incorporated by reference.

The present invention relates to the use of a cyclic undecapeptide for the preparation of a medicament for administration during a myocardial ischemic event.

Myocardial ischemias are defined as an imbalance between oxygen needs and supplies. This imbalance results in a disruption of cardiac function. In the vast majority of cases, myocardial ischemias are caused by an insufficiency of the blood circulation to the cardiac muscle tissue, thereby depriving the myocardial cells of oxygen supply or drastically reducing said oxygen supply. These ischemias may be due to the obstruction of a vessel (thrombosis) or to a reduction in the internal diameter of an artery (stenosis) or to a decrease in coronary blood flow (hypoperfusion) such as in conditions of circulatory insufficiency during severe sepsis with endotoxinemic shock. As regards the severe sepsis, it also leads to a hemodynamic dysfunction with direct myocardial depression.

Reperfusion is defined as the reestablishment of an adequate blood circulation in an ischemic tissue, making it possible to again reach the balance between oxygen needs and supplies. Reperfusion when there is complete interruption of coronary blood flow is effected by deobstruction of the occluded artery.

Infarctions occur subsequently to ischemias. The term "infarction" defines a delimited seat of tissue necrosis. Thus, myocardial infarction leads to the destruction of a part of the heart due to the death of cardiac muscle cells.

Myocardial infarction is a disease that is unfortunately very common. By way of example, in France, approximately 180 000 to 200 000 individuals per year are affected by this disease which is predominant in men. It appears, first and foremost, in individuals with cardiovascular risk factors such as smoking, obesity, diabetes, hyperlipidemia or arterial hypertension.

During severe sepsis, a myocardial hypoperfusion is accompanied by a direct myocardial depression. At the current time, it is not clear what mechanism that leads to a decrease in myocardial function is predominant (hypoperfusion or myocardial depression by circulating cytokines). Nevertheless, it is well known that patients with severe sepsis often suffer from cardiovascular deficiency with myocardial dysfunction.

Acute myocardial infarction (AMI) constitutes an absolute cardiological emergency which involves treatment by specialized medical and hospital units, the aim of treatment of the acute phase being to reperfuse the ischemic cardiac muscle and to prevent and/or limit the possible complications related to the infarction, which commonly result in death of the patients within the first hours or the first days.

The extent of the myocardial infarction is a determining element for the functional contractile recovery of the myocardium and for the long-term prognosis of the patients.

Although reperfusion unquestionably protects myocardial cells against cell death caused by the persistence of the ischemia, it is also accompanied by effects that are deleterious with respect to contractile function (myocardial stunning), heart rate (occurrence of arrhythmias) and tissue perfusion (no-reflow). Recent data even indicate that reperfusion can also paradoxically kill some of the reperfused cells (reperfusion necrosis).

During reperfusion of the myocardial infarction, medicaments belonging to different therapeutic classes, such as, for example, those of platelet aggregation inhibitors, for instance acetylsalicylic acid, that of beta blockers, that of angiotensin-converting enzyme inhibitors (ACEIs) or that of statins, have a beneficial effect on patient prognosis. However, none of these medicaments or other medicaments currently available which are administered during reperfusion is capable of limiting the size of the myocardial infarction.

On the other hand, repeat episodes of ischemia-reperfusion of short duration (which do not by themselves cause any irreversible cell lesion) carried out either before ("pre-conditioning") or after ("post-conditioning") the period of ischemia responsible for the infarction, have shown, in vivo, an endogenous protective effect and a limitation of the size of the infarction. However, pre-conditioning therapies are not applicable clinically to AMI patients for physiopathological and practical reasons. As regards post-conditioning treatments, they only apply to a limited number of patients with acute myocardial infarction, such as those that can be treated by percutaneous transluminal coronary angioplasty.

Although the cellular and enzymatic mechanisms involved in necrotic lesions of the myocardium due to ischemia-reperfusion have not been completely elucidated, Di Lisa et al. are of the opinion, in J. Biol. Chem., 2001, 276(4), 2571-2575, that the opening of pores located in the mitochondrial inner membrane, called mitochondrial permeability transition pores (MPTPs), plays a predominant role in myocardial cell death during reperfusion after ischemia. Thus, a direct or indirect inhibitory action of the opening of these MPTPs by a medicament such as cyclosporin A results in a decrease in the deleterious effect of the phenomena induced by an ischemia-reperfusion on cardiac tissue viability.

However, two points suggest that simply inhibiting MPTP, although necessary, is not sufficient to obtain a protective effect on the myocardium in the abovementioned ischemia-reperfusion situations. Firstly, MPTP inhibitors such as glutathione exist which show an additive effect with cyclosporin A on the inhibition of MPTP. However, protection against the phenomena induced by ischemia-reperfusion is nevertheless not obtained, or is only obtained if the treatment is combined with other protective factors like entrainment of the contractile function of the myocardium. Furthermore, timing of administration proposed by various authors in experimental models is questionable for obtaining beneficial effects induced by the inhibition of MPTP. The administration proposed in many experimental models corresponds to a continual perfusion of the heart before, during and after the period of ischemia, continuing throughout or during part of the reperfusion phase. This aspect of administration is not clinically applicable as it is, and the optimal method of administration is not known.

Thus, new adjuvant therapies which should be administered during the reperfusion, and the cardioprotective effect of which is to limit the size of the necrosis of the myocardium and to improve its function, are necessary in the treatment of certain myocardial ischemia-reperfusion events, in particular during an acute myocardial infarction and/or myocardial depression and dysfunction due to severe sepsis.

Furthermore, the window of time during which the medicament is administered is important. The administration of the medicament must imperatively begin before the reperfusion, and optionally continue during the latter, in order to obtain the benefit expected in terms of limitation of the size of the myocardial infarction, of muscle contractile recovery and of patient survival.

The aim of the present invention is to provide the clinician with a medication which allows him or her to treat certain myocardial ischemic events, in particular during an acute infarction and/or subsequent to severe sepsis, in treatment adjuvant to myocardial reperfusion, and which has the effect of limiting the size of the infarction and of improving its function.

It has been found, very surprisingly, that the same can be achieved using a specific cyclic undecapeptide.

Thus, a subject of the present invention is the use of a cyclic undecapeptide having the structure of formula (I)

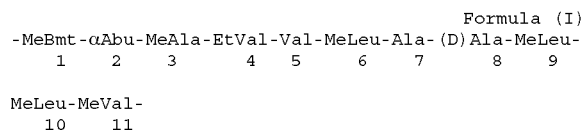

for the preparation of a medicament for administration during a myocardial ischemic event.

Since the chemical structure of the cyclic undecapeptide of formula (I) has a certain number of points common with that of cyclosporin A, its formula is given using the nomenclature normally used to characterize this cyclosporin A. According to this nomenclature, MeBmt is the abbreviation for the amino acid N-methyl-(4R)-4-but-2E-en-1-yl-4-methyl-(L)-threonine, αAbu that for L-α-aminobutyric acid, MeAla that for N-methyl-L-alanine, EtVal that for N-ethyl-L-valine, Val that for valine, MeLeu that for N-methyl-L-leucine, Ala that for L-alanine, (D)Ala that for D-alanine and MeVal that for N-methyl-L-valine. The numbering normally used to characterize the respective position of each of the amino acids constituting cyclosporin A is also used to define the structure of the cyclic undecapeptide of formula (I). Still with reference to cyclosporin A, the cyclic undecapeptide of formula (I) can also be referred to as $[MeAla]^3$-$[EtVal]^4$-CsA.

The cyclic undecapeptide having the structure of formula (I) and its preparation have been described by J. F. Guichoux in "De nouveaux analogues de Cyclosporin A comme agent anti-HIV-1" ["Novel cyclosporin A analogs as anti-HIV-1 agent"], doctoral thesis, Science Faculty of the University of Lausanne, 2002, and by R. Wenger et al., in international patent application WO 00/01715, and the registration number assigned to it by Chemical Abstracts Service is CAS RN 254435-95-5.

This product, and also some of its structural analogs, are presented in these publications as having a strong activity in terms of inhibiting the action of the human immunodeficiency virus, the viral agent responsible for AIDS, while at the same time not having the well-known immunosuppressive properties of cyclosporin A. Furthermore, this product has also been recognized as having a neuroprotective potential, in particular the inhibition of MPTP of mitochondria isolated from the brain, by Hansson et al., in J. Bioenerg. Biomembr., 2004, 36, 407-413.

Myocardial ischemic events, during which the cyclic undecapeptide of formula (I) can be administered, result from a decrease in or the interruption of myocardial blood flow, the consequence of which is, inter alia, a reduction or the interruption of the oxygen supply to this organ, requiring reestablishment of the blood flow or cardiac reperfusion. These ischemic events can manifest themselves in terms of cardiac dysfunctions detectable, inter alia, by echo- and electrocardiography. This phenomenon results in cardiac cell lesions detectable, inter alia, by measuring biological markers such as cardiac enzymes, medical imaging such as echography, nuclear scintigraphy or nuclear magnetic resonance.

An acute, subacute or chronic myocardial ischemia can be brought about by, or associated with, a variety of factors or diseases. Among these factors or diseases, mention may be made, for example, of acute myocardial infarction, angina pectoris, unstable angina, atheromatous diseases with thromboembolism, vasospasms, aneurisms of the small and medium arteries and of the large vessels, arterial hypotension due to a heart or systemic disease, including serious infections such as a severe sepsis with or without septic shock or allergic reactions, and hypotension due to the effect of one or more medicaments, drugs, poisons or toxic products.

Furthermore, mention may also be made, by way of example, of secondary hypoperfusions subsequent to one or other of the following diseases or events: sugar diabetes, hyperlipidemia, thromboangiitis obliterans or Buerger's disease, Takayasu's syndrome, cardiovascular syphilis, connective tissue disorders such as Raynaud's disease, phlegmasia caerulea dolens or Grégoire's blue phlebitisy blood vessel trauma including iatrogenic traumas such as surgical or organ transplant procedures, and heart operations and operations on the large vessels with or without the use of extracorporeal circulation techniques. These procedures also include, by way of example, the surgical insertion of implants, of devices, of grafts, of prostheses or any other device or biomedical product, in particular cardiological. A nonlimiting list of the organs or tissues in which these ischemic events may occur include the heart, the brain, the kidneys, the extremities, the spleen, the liver, the stomach and the gastrointestinal system, including the small intestine, the colon and the rectum, the lungs and the respiratory pathways, the eyes, the skin, the muscles, the pancreas, the prostate, the bone marrow and the endocrine glands.

The use of the cyclic undecapeptide of formula (I) is particularly suitable for the treatment of myocardial ischemic events, for the treatment of a myocardial hypoperfusion-reperfusion, in particular during the occurrence of an acute myocardial infarction and/or of cardiac dysfunction during severe sepsis.

When the cyclic undecapeptide of formula (I) is used, the treatment of the myocardial ischemia-related events consists in administering said cyclic undecapeptide to the individual prior to and/or during the reestablishment of blood flow or a perfusion appropriate for the oxygen needs in the heart or the cardiac tissue. Thus, the blood circulation is reestablished by means of a reperfusion obtained mechanically by coronary angioplasty and/or medically following a fibrinolysis treatment and/or following drug-based reanimation steps. The cyclic undecapeptide of formula (I) is preferably administered prior to said reperfusion. In this case, the beginning of the administration is spread out over a period preferably ranging from the thirtieth minute preceding the reperfusion, more preferably over the 10 minutes preceding this reperfusion, more preferably over the 5 minutes preceding this reperfusion, more preferably over the minute preceding this reperfusion, up to the moment when the artery is reopened and/or from the reestablishment of blood flow.

When treatment of a sepsis is involved, the beginning of the administration of said cyclic undecapeptide of formula (I) takes place in a period from preferably, at the earliest, when this sepsis sets in, and preferably, at the latest, 72 hours.

The pharmaceutical preparation comprising the derivative is administered by intravenous, intraarterial, intracoronary or intramyocardial injection, preferably as a bolus and/or followed by continuous infusion for the ten hours which follow the beginning of the reperfusion. The administration of the pharmaceutical preparation as a continuous infusion can then be carried out by intravenous injection or by intraarterial injection.

When the reestablishment of blood flow is initiated with drugs, the administration of the cyclic undecapeptide of formula (I) can be carried out separately from and/or prior to and/or concomitantly with this drug administration and can be continued during this drug administration and then for the ten hours which follow the reestablishment of blood flow. The pharmaceutical preparation comprising the cyclic undecapeptide of formula (I) can then be administered as a single dose by intravenous injection, preferably as a bolus, and then the administration can be continued as a continuous infusion for the ten hours which follow the beginning of the reperfusion.

The pharmaceutical composition comprising the cyclic undecapeptide of formula (I) as active compound is in the form of a solution or a dispersion, or in the form of injectable deposit formulations. These formulations can comprise the active compound in the form of nanocrystals, micelles, lipid emulsions, microemulsions or nanoparticulate suspensions. The pharmaceutical compositions for injectable solutions comprise said undecapeptide in combination with at least one pharmaceutically acceptable carrier. Before the administration, the concentrated compositions are combined with suitable diluents, comprising at least one excipient, such as an isotonic agent, a buffer or another pH modifier, and a preserving agent. These excipients can be added so as to keep the composition within a pH range of approximately 5.5 to approximately 8.5 and within an osmolarity range of approximately 280 to approximately 400 mosm/l. In general, the formulations normally used for the preparation of a cyclosporin A-based medicament are also suitable for implementing the present invention.

The use of the cyclic undecapeptide of formula (I) can also be carried out as a supplement to a standard anti-angina treatment (beta blocker, delayed-action nitro derivative, calcium antagonist, antiplatelet agent) and/or to a treatment for septic shock. The administration of the undecapeptide is then either concomitant with or sequential to at least a second compound that is active in said treatments.

Preferably, during the treatment of a myocardial ischemia-reperfusion, the cyclic undecapeptide of formula (I) is administered at a dose ranging from 0.1 mg/kg to 30 mg/kg, preferably from 0.1 mg/kg to 20 mg/kg.

The specialist knows how to establish the method of administration, equally in terms of the timing, the mode of administration or the dose, such that an effective concentration of the cyclic undecapeptide reaches the hypoperfused cardiac tissue from the first seconds of the reperfusion onward.

The invention and all its effects will be explained in detail by means of the drawing and the examples.

Figure 2:
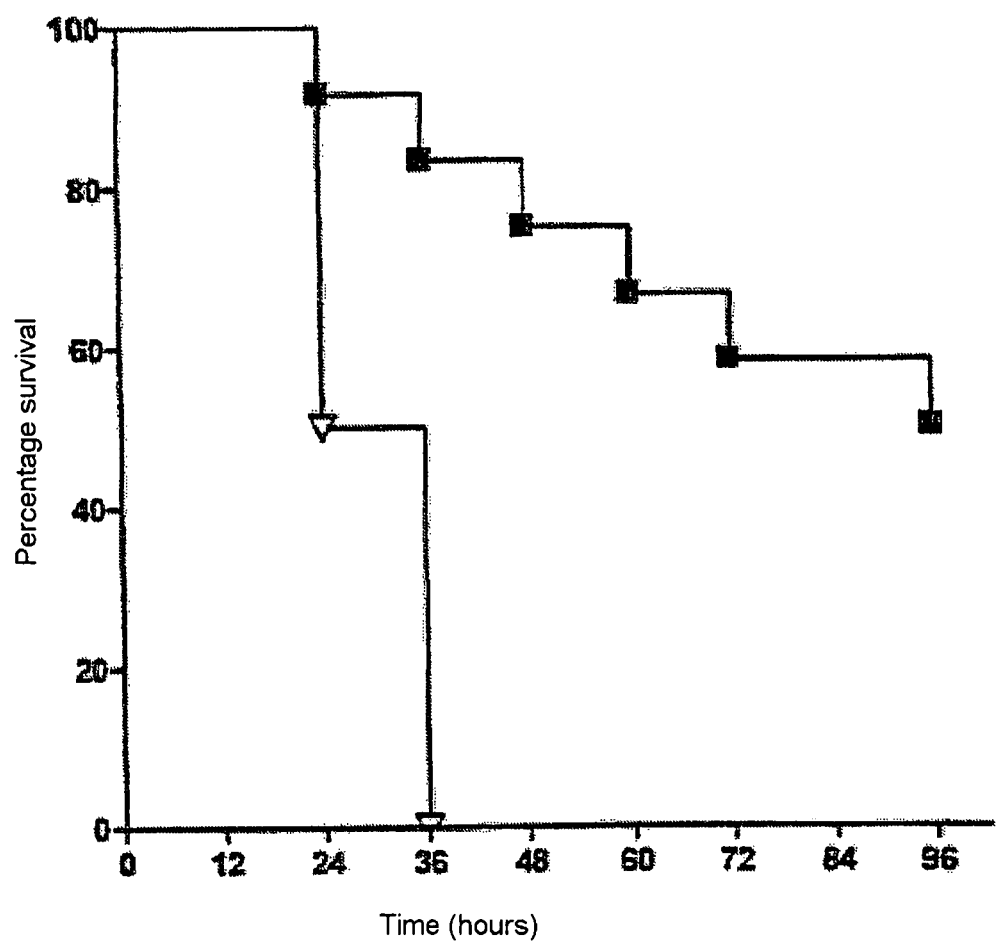

In the drawing:

FIG. 1 represents the survival curves of an ischemia-reperfusion model in the mouse and the influence of the cyclic undecapeptide of formula (I) on the post-infarction period. The dark curve represents the survival rate over time of the mice treated with the pharmaceutical carrier alone after reperfusion and the light curve represents the survival rate over time of the mice treated with the undecapeptide of the invention; and FIG. 2 represents the survival curves of a septic shock model in the mouse and the influence of the cyclic undecapeptide of formula (I) on the post-septic period. The curve with the triangles represents the survival rate over time of the mice treated with physiological saline only, after induction of the septic shock, and the curve with the squares, the mice treated with the undecapeptide of the invention.

During the examples which follow, the following formulation was used:

| cyclic undecapeptide of formula (I) | 35 mg/ml, |
| chromophore EL | 650 mg/ml, |
| ethanol | 261 mg/ml. |

EXAMPLE 1

Model of Ischemia-Reperfusion in the Rabbit—Cardioprotective Effect of the Cyclic Undecapeptide of Formula (I)

The aim of this study is to test the cardioprotective effect of the cyclic undecapeptide of formula (I), otherwise referred to as $[MeAla]^3$-$[EtVal]^4$-CsA, in terms of reduction in the size of the myocardial infarction measured 4 hours after the occurrence of the infarction.

After tracheotomy and ventilation with ambient air, a thoracotomy is performed in the fourth left intercostal space. A marginal branch of the left circumflex coronary artery is ligatured using a 3.0 silk suture thread. During the procedure, the temperature, the heart rate and the blood pressure are controlled. After occlusion for 30 minutes, the ligature is released (reperfusion) and the animals are kept in a controlled atmosphere for 4 hours before euthanasia.

One group of animals receives the pharmaceutical carrier for $[MeAla]^3$-$[EtVal]^4$-CsA, another group is treated with $[MeAla]^3$-$[EtVal]^4$-CsA intravenously in the form of a single injection respectively of 20 mg/kg, one minute before the ligature is released. Four hours after the reperfusion, the coronary artery is briefly reoccluded and a blue dye is injected intravenously so as to determine the zone at risk. The animals are anesthetized and the excised heart is cut into 5 or 6 thin slices which are weighed. The basal surface of these slices is photographed. Incubation of these slices in 2,3,5-triphenyltetrazolium for 5 minutes at 37° C. makes it possible to differentiate the live (brick red) and necrosed (pale yellow) zones of the myocardium. The slices are photographed. The areas of the zones at risk and of the infarcted myocardium or area of necroses are determined by planimetry. The size of the infarction and the size of the zone at risk are calculated and expressed as percentage of left ventricular weight.

TABLE 1

Size of the myocardial infarction determined in terms of the ratio of the areas of necroses (AN) to the areas of zones at risk (AR) as percentage. SD represents the standard deviation.

| Compound | Number of animals per group | Infarction size (AN/AR ± SD) [%] |
| --- | --- | --- |
| Pharmaceutical carrier | 10 | 49 ± 9.5 |
| $[MeAla]^3$-$[EtVal]^4$-CsA | 8 | 29 ± 6.0 |

It was noted that the use of $[MeAla]^3$-$[EtVal]^4$-CsA makes it possible to obtain a decrease in the size of the infarction in the zone at risk that is of the order of 40% compared with the animals having received only the pharmaceutical carrier.

EXAMPLE 2

Model of Ischemia-Reperfusion in the Mouse—Influence of [MeAla]³-[EtVal]⁴-CsA on the Post-Infarction Period (Ventricular Remodeling and Survival)

After anesthesia, the mice are intubated and ventilated with a rodent ventilator. The rectal temperature is controlled and maintained at 38°-39° C. After sternotomy, the anterior interventricular artery is ligatured with an 8-0 polypropylene thread. The ischemia is visualized through the appearance of an elevated ST segment on the ECG (electrocardiogram) and the paleness of the myocardium. After 25 minutes of occlusion, the ligature is released and the reperfusion is verified by visual inspection and disappearance of the upshift in the ST segment. The thoracic wall is closed by suturing and the mice are kept in a controlled-temperature atmosphere.

One group of animals receives the carrier for [MeAla]³-[EtVal]⁴-CsA; another group is treated with [MeAla]³-[EtVal]⁴-CsA by intravenous injection (single injection at 10 mg/kg), 3 minutes before the ligature is released. The animals are monitored for 30 days and the mortality is reported for each group.

Four weeks after the reperfusion, the left ventricular remodeling is studied by Doppler echocardiography and the left ventricular ejection fraction is measured.

The zone at risk and the size of the infarction are determined in a group of animals that have undergone 25 minutes of coronary occlusion followed by 24 hours of reperfusion. After a brief reocclusion of the anterior interventricular artery, a blue dye is injected via the vena cava so as to determine the zone at risk. The animals are anesthetized and the heart is excised. The ventricle is cut into 5 thin slices and photographed. Incubation of these slices in 2,3,5-triphenyltetrazolium for 15 minutes at 37° C. makes it possible to differentiate the live (brick red) and necrosed (pale yellow) zones of the myocardium. The slices are photographed. The areas of the zones at risk and of the infarcted myocardium are determined by planimetry. The size of the infarction and the size of the zone at risk are calculated and expressed as percentage of left ventricular weight.

TABLE 2

Size of the myocardial infarction determined in terms of the ratio of the areas of necroses (AN) to the areas of the zones at risk (AR) as a percentage 24 hours after reperfusion. SD represents the standard deviation.

| Compound | Number of animals per group | Infarction size (AN/AR ± SD) [%] |
|---|---|---|
| Pharmaceutical carrier | 10 | 61.4 ± 5.8 |
| [MeAla]³-[EtVal]⁴-CsA | 7 | 32.1 ± 7.3 |

TABLE 3

Left ventricular remodeling studied by Doppler echocardiography: left ventricular ejection fraction 4 weeks after reperfusion. SD represents the standard deviation.

| Compound | Number of animals per group | Left ventricular ejection fraction ± SD [%] |
|---|---|---|
| Pharmaceutical carrier | 10 | 62 ± 12 |
| [MeAla]³-[EtVal]⁴-CsA | 14 | 77 ± 6 |

It was noted that the use of [MeAla]³-[EtVal]⁴-CsA makes it possible to obtain a decrease in the size of the infarction in the zone at risk that is of the order of 50% (table 2). Furthermore, a decrease in the mortality rate at 4 weeks (FIG. 1) and also a better myocardial function, expressed through an increase in the ejection fraction (table 3), were recorded.

It is found, surprisingly, that these beneficial effects, for the same dose of active compound, are not obtained when the administration of the undecapeptide of the invention is carried out too early or too late relative to the reperfusion.

EXAMPLE 3

Model of Septic Shock in the Mouse—Influence of [MeAla]³-[EtVal]⁴-CsA on the Survival of Septicemic Mice with a Myocardial Dysfunction After the mice had been anesthetized, a peritonitis is induced by cecal ligature and puncture, as follows: a median laparotomy is performed, the cecum is lifted out and a single puncture of said cecum is performed below the ileocecal valve with a 21-gauge needle. The cecum is put back into the abdominal cavity, which is then sutured in 2 planes. After the mice have come round, they are given a parenteral injection of the analgesic nalbuphine.

One group of animals receives physiological saline (control group); another group is treated with [MeAla]³-[EtVal]⁴-CsA at a rate of 10 mg/kg by parenteral injection just after surgical induction of septic shock. The animals are monitored for 4 days and the mortality is reported for each group.

FIG. 2 represents the improvement in survival of the septicemic mice treated with [MeAla]³-[EtVal]⁴-CsA compared with the animals of the control group. 72 hours after induction of the sepsis and beginning of the treatment, the survival rate for the treated animals is approximately 60% compared with the animals of the control group, in which 100% mortality is reached in 36 hours. This effect can be explained essentially by the cardioprotective effect of [MeAla]³-[EtVal]⁴-CsA on the myocardial dysfunction.

What is claimed is:

1. A method of treating a myocardial ischemic event in an individual using a non-immunosuppressive cyclic undecapeptide having the structure of formula (I)

comprising administering said cyclic undecapeptide to the individual prior to and/or during reestablishment of blood flow or perfusion appropriate for an oxygen need in a heart or a cardiac tissue of said individual.

2. The method as claimed in claim 1, wherein said myocardial ischemic event manifests itself in terms of a cardiac dysfunction.

3. The method as claimed in claim 2, wherein said cardiac dysfunction is the consequence of cardiac cell lesions.

4. The method as claimed in claim 1, wherein said myocardial ischemic event is encountered with a disease selected from the group consisting of: acute myocardial infarction, angina pectoris, unstable angina, atheromatous diseases with thromboembolism, vasospasms, aneurisms of the small and medium arteries and of the large vessels, arterial hypotension due to a heart or systemic disease, serious infections, severe sepsis with or without septic shock or allergic reactions, and hypotension due to the effect of one or more medicaments, drugs, poisons or toxic products.

5. The method as claimed in claim 1, wherein the blood circulation is reestablished by means of a reperfusion obtained mechanically by coronary angioplasty and/or medically following a fibrinolysis treatment and/or following drug-based reanimation steps, and comprising administering non-immunosuppressive cyclic undecapeptide of formula (I) prior to said reperfusion.

6. The method as claimed in claim 5, wherein the beginning of the administration of said non-immunosuppressive cyclic undecapeptide of formula (I) is spread over a period ranging from the thirtieth minute preceding the reperfusion up to the moment when the artery is reopened and/or from the reestablishment of blood flow.

7. The method as claimed in claim 6, wherein the beginning of the administration of said non-immunosuppressive cyclic undecapeptide of formula (I) takes place in a period from, at the earliest, when the sepsis sets in and, at the latest, 72 hours.

8. The method as claimed in claim 1, comprising administering said non-immunosuppressive cyclic undecapeptide of formula (I) at a dose ranging from 0.1 mg/kg to 30 mg/kg.

9. The method as claimed in claim 1, comprising coadministering or administering separately said non-immunosuppressive cyclic undecapeptide of formula (I) with or from, respectively, at least a second compound that is active in anti-angina and/or anti-sepsis treatment.

10. The method as claimed in claim 1, comprising administering said non-immunosuppressive cyclic undecapeptide of formula (I) by intravenous, intraarterial or intracoronary injection.

11. A method of treating a myocardial ischemic event in an individual using a non-immunosuppressive cyclic undecapeptide having the structure of formula (I)

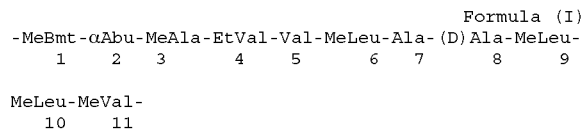

comprising coadministering to the individual said cyclic undecapeptide and at least a second compound that is active in anti-angina and/or anti-sepsis treatment prior to and/or during reestablishment of blood flow or perfusion appropriate for an oxygen need in a heart or a cardiac tissue of said individual.

12. The method as claimed in claim 11, wherein said myocardial ischemic event manifests itself in terms of a cardiac dysfunction.

13. The method as claimed in claim 12, wherein said cardiac dysfunction is the consequence of cardiac cell lesions.

14. The method as claimed in claim 11, wherein said myocardial ischemic event is encountered with a disease selected from the group consisting of: acute myocardial infarction, angina pectoris, unstable angina, atheromatous diseases with thromboembolism, vasospasms, aneurisms of the small and medium arteries and of the large vessels, arterial hypotension due to a heart or systemic disease, serious infections, severe sepsis with or without septic shock or allergic reactions, and hypotension due to the effect of one or more medicaments, drugs, poisons or toxic products.

15. The method as claimed in claim 11, wherein the blood circulation is reestablished by means of a reperfusion obtained mechanically by coronary angioplasty and/or medically following a fibrinolysis treatment and/or following drug-based reanimation steps, and comprising administering said non-immunosuppressive cyclic undecapeptide of formula (I) prior to said reperfusion.

16. The method as claimed in claim 15, wherein the beginning of the administration of said non-immunosuppressive cyclic undecapeptide of formula (I) is spread over a period ranging from the thirtieth minute preceding the reperfusion up to the moment when the artery is reopened and/or from the reestablishment of blood flow.

17. The method as claimed in claim 16, wherein the beginning of the administration of said non-immunosuppressive cyclic undecapeptide of formula (I) takes place in a period from, at the earliest, when the sepsis sets in and, at the latest, 72 hours.

18. The method as claimed in claim 11, comprising administering said non-immunosuppressive cyclic undecapeptide of formula (I) at a dose ranging from 0.1 mg/kg to 30 mg/kg.

19. The method as claimed in claim 11, comprising administering said non-immunosuppressive cyclic undecapeptide of formula (I) by intravenous, intraarterial or intracoronary injection.

* * * * *